US00PP26304P3

(12) United States Plant Patent
Lee

(10) Patent No.: US PP26,304 P3
(45) Date of Patent: Jan. 12, 2016

(54) ***RHODODENDRON* PLANT NAMED 'HOMLEE'**

(50) Latin Name: ***Rhododendron* hybrid**
Varietal Denomination: HOMLEE

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 175 days.

(21) Appl. No.: 13/998,450

(22) Filed: Oct. 30, 2013

(65) Prior Publication Data

US 2015/0121585 P1 Apr. 30, 2015

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Anne Grunberg
(74) *Attorney, Agent, or Firm* — Cassandra Bright

(57) ABSTRACT

A new and distinct *Rhododendron* cultivar named 'HOMLEE' is disclosed, characterized by distinctive fuchsia pink, semi-double flowers. Plant form is distinctively upright, with branches occurring at acute angles. Plants bloom Spring, Summer and Fall. The new cultivar is a *Rhododendron*, suitable for ornamental garden purposes.

2 Drawing Sheets

Figure 1:
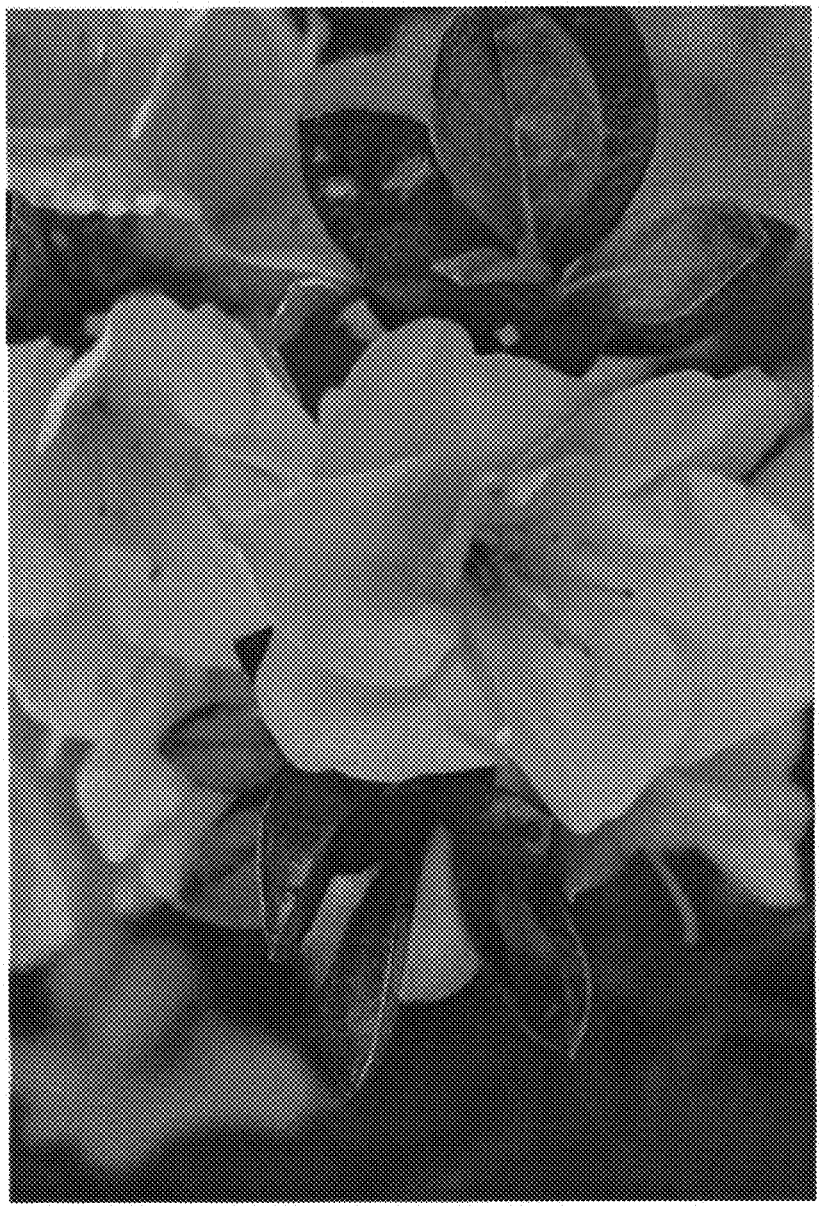

Latin name of the genus and species: *Rhododendron* hybrid.

Variety denomination: 'HOMLEE'.

BACKGROUND OF THE INVENTION

The new cultivar is a product of a planned breeding program by the inventor. This new variety, hereinafter referred to as 'HOMLEE', was discovered as a seedling resulting from a pollination of *Rhododendron* 'Princess Ruth', unpatented with an unnamed, unpatented *Rhododendron oldhamii* by the inventor, Robert Edward Lee, in Independence, La., at a research nursery.

After identifying the new variety as a potentially interesting selection, the inventor first organized propagation of 'HOMLEE' by vegetative cuttings during 2004 at the same commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'HOMLEE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HOMLEE' These characteristics in combination distinguish 'HOMLEE' as a new and distinct *Rhododendron* cultivar:

1. Unique Spring, Summer and Fall blooming
2. Deep, bright pink flower
3. Semi double flowers 4. Easily propagated with semi-hardwood cuttings in late spring through summer
5. Vigorous growth under normal fertilization and moisture conditions
6. Upright growth nature
7. Good specimen plant
8. Good container plant
9. Hardy to USDA Zone 7
10. Attracts butterflies

COMPARISON TO PARENT VARIETY

'HOMLEE' is similar in most horticultural characteristics to the seed parent variety *Rhododendron* hybrid 'Princess Ruth' unpatented. Plants of the new cultivar 'HOMLEE' however, produce flowers that are brighter pink in coloration, than the seed parent variety. Additionally, plant habit is overall more uprgith in the new variety, than the parent.

'HOMLEE' is similar in most horticultural characteristics to the pollen parent variety *Rhododendron oldhamii* unpatented. Plants of the new cultivar 'HOMLEE' however, produce flowers that are fuchsia pink in coloration, compared more red toned flowers of the pollen parent. Additionally, flowers of the new variety are typically double, whereas the pollen parent produces single flowers. Plant structure of the new variety is highly compact and upright, with branches arising at acute angles. The pollen parent plant is open and rangy.

COMMERCIAL COMPARISON

'HOMLEE' can be compared to the commercial variety *Rhododendron* 'Red Slippers', unpatented. Plants of the new cultivar 'HOMLEE' are similar to plants of 'Red Slippers' in most horticultural characteristics, however, plants of the new cultivar 'HOMLEE' produce flowers that are fuchsia pink in coloration, compared more red toned flowers of this comparator. Additionally, plant formation of 'HOMLEE' is distinctly upright, whereas the plant habit of 'Red Slippers' is mounding.

BRIEF DESCRIPTION OF THE PHOTOGRAPHS

The accompanying photograph in FIG. 1 illustrates in full color a close up of typical flowers of the new variety.

Figure 2:
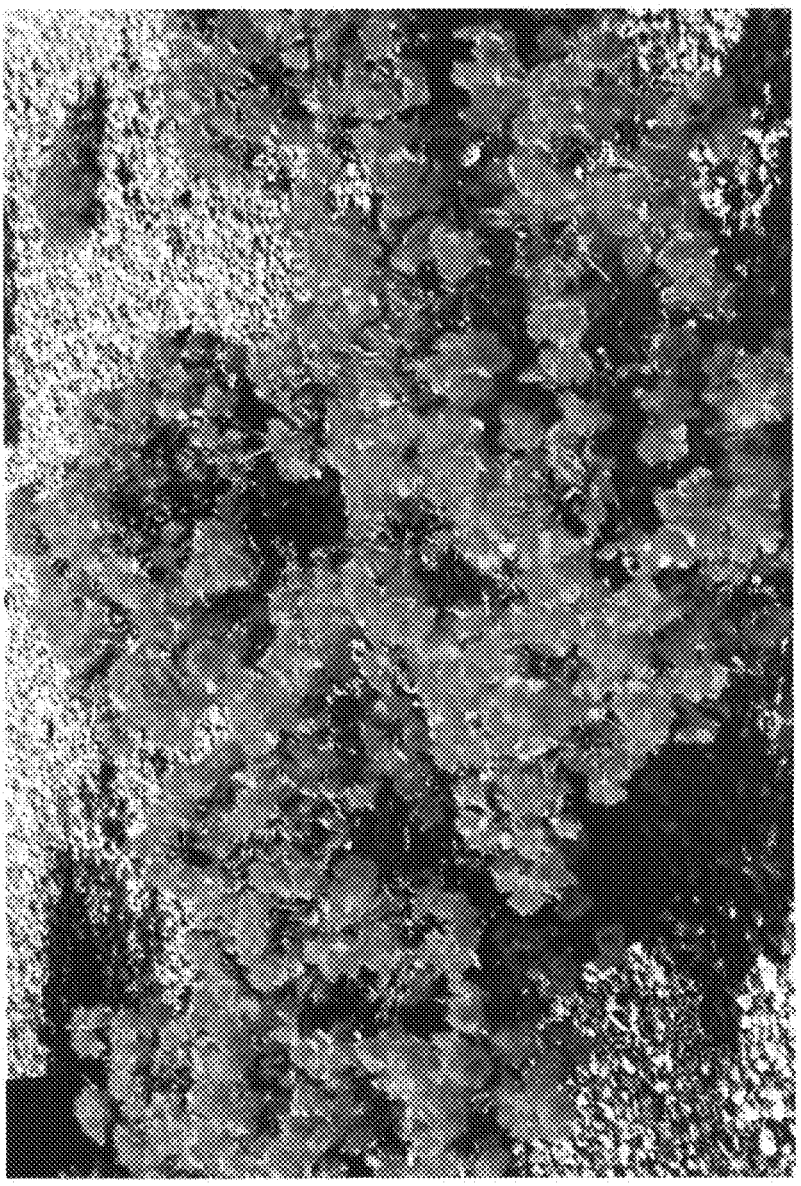

FIG. 2 shows a plant of 'HOMLEE' grown outdoors in Alabama.

The plant is approximately 2 years old, and is shown in a three gallon container. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HOMLEE' plants grown outdoors in Loxley, Ala. Plants are approximately 3 years old, in a 3 gallon nursery container. Measurements and numerical values represent averages of typical plant types.

Botanical classification: *Rhododendron* hybrid 'HOMLEE'.

PROPAGATION

Typically by semi-hardwood cuttings in Spring and Summer.

Root description: Fine, fibrous young roots, well branched. Colored near RHS Grey-Brown 199A.

PLANT

Growth habit: Narrow, upright shrub.

Height: Approximately 43 cm to top of foliar and flowering plane.

Plant spread: Approximately 45 cm.

Branching characteristics: Well branched, approximately 6 primary branches from the center of the plant. Branches occur at approximately 45° angles. Each primary branch has 4 to 8 lateral branches.

Primary branches:

- *Length of primary branches.*—Average 32 cm.
- *Diameter of primary branches.*—Approximately 0.6 cm.
- *Primary branch strength.*—Very strong, difficult to break.
- *Primary branch color.*—Near RHS Greyed-Orange 164A, with age, covered with a thin bark like layer colored near Brown 200B.
- *Primary branch texture.*—Young growth hirsute, hairs, approximately 0.15 cm long, colored near Yellow-Green 152C. Older growth scaly, hirsute. Hairs colored near White 155D.

Lateral branches:

- *Number of lateral branches.*—Approximately 4 to 10 per primary branch.
- *Length of lateral branches.*—Average 9 cm.
- *Diameter of lateral branches.*—Average 0.4 cm.
- *Lateral branch strength.*—Very strong, flexible.
- *Lateral branch color.*—Near RHS Yellow-Green N144A, flushed with Greyed-Orange 165B.
- *Lateral branch texture.*—Hirsute.
- *Internode length.*—Average 1.2 cm.
- *Age of plant described.*—Approximately 2 years.

FOLIAGE

Leaf:

- *Type.*—Simple.
- *Arrangement.*—Alternate.
- *Average length.*—Approximately 4.1 cm.
- *Average width.*—Approximately 1.7 cm.
- *Shape of blade.*—Broad elliptic.
- *Apex.*—Acute.
- *Base.*—Broad attenuate.
- *Attachment.*—Stalked.
- *Margin.*—Entire.
- *Texture of top surface.*—Pubescent: Hairs appressed.
- *Texture of bottom surface.*—Pubescent. More hairs present along main vein and margin.
- *Color.*—Young foliage upper side: Near RHS Green 137B. Young foliage under side: Near RHS Green 138A. Mature foliage upper side: Near RHS Green 137A, but darker. Mature foliage under side: Near RHS Green 138A.
- *Venation.*—Type: Pinnate. Venation color upper side: Near RHS Yellow-Green 144C. Venation color under side: Near RHS Yellow-Green N144A.
- *Petiole.*—Length: About 0.9 cm. Diameter: About 0.25 cm. Color: Upper Surface: Near RHS Yellow-Green 144C. Lower Surface: Near RHS Yellow-Green 144C.

FLOWER

Bloom period: Plants flower in the Spring, then begin intermittent flowering cycles in late Spring/Summer through Fall.

Flower:

- *Arrangement.*—Axillary clusters of perfect, open funnel shaped individual flowers. Typically 4 to 10 flowers per cluster.

Inflorescence:

- *Height.*—Average 12.0 cm.
- *Diameter.*—Average 14.0 cm.

Peduncle:

- *Length.*—Average 1.9 cm.
- *Diameter.*—0.3 cm.
- *Color.*—Near RHS Yellow-Green N144A.
- *Texture.*—Densely pubescent.
- *Aspect.*—Straight to very slightly curved. Angle of attachment, approximately 35° angle from stem.

Flowers:

- *Length.*—Average 4.8 cm.
- *Diameter.*—Average 7.1 cm.
- *Facing direction.*—Outwardly and upwardly facing.
- *Persistent or self-cleaning.*—Petals self-cleaning.
- *Fragrance.*—None.
- *Tube.*—Tube length: Approximately 1.7 cm. Tube width a widest point: Approximately 1.9 cm. Tube width and narrowest point: Approximately 0.9 cm.
- *Petals.*—Unfused petal segments: Length: Approximately 2.7 cm. Width: Approximately 2.8 cm. Apex: Blunt, rounded with shallow, irregular lobes. Shape of petal: Unfused portion, obovate. Petal margin: Entire. Petal Arrangement: Approximately ⅓ fused from base. Petal Number: 5. Petal Texture: Smooth. Color:

Upper surface at first opening: Near RHS Red 53B. Under surface at first opening: Near RHS Red 53D. Inner surface at maturity: Near RHS Red-Purple 61B. Outer surface at maturity: Near RHS Red-Purple 60D. Upper surface at fading: Near RHS Red-Purple 60D. Under surface at fading: Near RHS Red-Purple 60D.

Bud:

*Shape*.—Elliptic.
*Length*.—3.1 cm.
*Diameter*.—1.2 cm.
*Color*.—Near RHS Red 53A.

Calyx/sepals:

*Quantity per flower*.—5 sepals.
*Shape*.—Narrow deltate.
*Length*.—0.8 cm.
*Width*.—0.3 cm.
*Apex*.—Acute.
*Base*.—Fused.
*Margin*.—Entire.
*Texture*.—Highly pubescent. Color: Inner Surface: Near RHS Green 137A. Outer Surface: Near RHS Green 137A.

REPRODUCTIVE ORGANS

Stamens:

*Number*.—10.
*Length*.—3.4 cm.
*Width*.—0.1 cm.
*Color*.—Near RHS Red-Purple 58A.
*Anthers*.—Length: Approximately 0.3 cm. Color: Near RHS Red 53A. Pollen: Scant, colored near Greyed-Orange 164D.

Pistil:

*Number*.—1.
*Length*.—4.8 cm.
*Style*.—Length: 4.4 cm. Color: Near RHS Red-Purple 58A.
*Stigma*.—Globular, colored near Red-Purple 60C.
*Ovary*.—Sericeous texture. Approximately 0.3 cm in diameter. Colored near Red-Purple 60D.

OTHER CHARACTERISTICS

Disease and pest resistance: Not observed to be susceptible nor resistant to normal diseases and pests of *Rhododendron* hybrid.

Temperature tolerance: USDA Zone 6.

Fruit/seed production: Not observed to date.

What is claimed is:

1. A new and distinct cultivar of *Rhododendron* plant named 'HOMLEE' as herein illustrated and described.

* * * * *